United States Patent
Gerold

(10) Patent No.: US 9,757,224 B2
(45) Date of Patent: *Sep. 12, 2017

(54) COBALT ALLOY FOR MEDICAL IMPLANTS AND STENT COMPRISING THE ALLOY

(71) Applicant: Biotronik AG, Buelach (CH)

(72) Inventor: Bodo Gerold, Karlstadt (DE)

(73) Assignee: BIOTRONIK AG, Buelach (CH)

( * ) Notice: Subject to any disclaimer, the term of this patent is extended or adjusted under 35 U.S.C. 154(b) by 547 days.

This patent is subject to a terminal disclaimer.

(21) Appl. No.: 13/910,326

(22) Filed: Jun. 5, 2013

(65) Prior Publication Data

US 2013/0338757 A1     Dec. 19, 2013

Related U.S. Application Data

(60) Provisional application No. 61/660,824, filed on Jun. 18, 2012.

(51) Int. Cl.
| | | |
|---|---|---|
| *A61F 2/06* | (2013.01) | |
| *C22C 19/07* | (2006.01) | |
| *C22F 1/10* | (2006.01) | |
| *A61L 31/02* | (2006.01) | |

(52) U.S. Cl.
CPC ............. *A61F 2/06* (2013.01); *A61L 31/022* (2013.01); *C22C 19/07* (2013.01); *C22F 1/10* (2013.01)

(58) Field of Classification Search
CPC .............................. A61L 31/022; C22C 19/07
USPC .................................................. 420/550, 585
See application file for complete search history.

(56) References Cited

U.S. PATENT DOCUMENTS

| | | | |
|---|---|---|---|
| 2,977,224 A | 3/1961 | Faulkner | |
| 3,713,175 A | 1/1973 | Weisman | |
| 3,837,838 A | 9/1974 | Mohammed | |
| 3,865,585 A | 2/1975 | Rademacher | |
| 4,116,724 A * | 9/1978 | Hirschfeld | C22C 19/07 148/425 |
| 5,002,731 A * | 3/1991 | Crook | C22C 32/00 148/425 |
| 6,756,012 B2 * | 6/2004 | Prasad | A61K 6/046 148/425 |
| 2013/0336836 A1 * | 12/2013 | Gerold | A61L 31/022 420/440 |

FOREIGN PATENT DOCUMENTS

| | | | |
|---|---|---|---|
| DE | 3624377 A1 | 1/1988 | |
| DE | 19704530 A1 | 8/1998 | |
| EP | 1 604 692 | 2/2005 | |
| EP | 1 604 691 | 3/2008 | |
| GB | 2 230 536 | 10/1990 | |
| WO | WO 0172349 A1 * | 10/2001 | ........... A61L 31/022 |

OTHER PUBLICATIONS

Huibregste, Barbara, et al., "New DES Platforms. Does the metal alloy matter?", *Cardiac Interventions Today*, Jul./Aug. 2011, pp. 35-39.
Onozuka et al, "Double HCP Phase in Cobalt Alloys With Dilute Contents of Iron," Journal of the Physical Society of Japan 37 (Sep. 1974) 687-693.
Remy et al., "Twinning and Strain-Induced F.C.C. → H.C.P. Transformation on the the Mechanical Properties of Co—Ni—Cr—Mo Alloys," Material Science and Engineering 26 (May 1976) 123-132.

* cited by examiner

*Primary Examiner* — Jie Yang
(74) *Attorney, Agent, or Firm* — Greer, Burns & Crain, Ltd.; Steven P. Fallon

(57) ABSTRACT

An embodiment of the invention relates to a cobalt-based alloy, which due to the composition exhibits twinning as the dominating deformation mechanism:

Cr: 13.0 to 30.0% by weight
Mn: 2.0 to 10.0% by weight
W: 2.0 to 18.0% by weight
Fe: 5.0 to 15.0% by weight
C: 0.002 to 0.5% by weight
N: 0 to 0.2% by weight
Si: 0 to 2.0% by weight
Ni: 0 to 5.0% by weight wherein the aforementioned alloying components and manufacturing-related impurities add up to 100% by weight, and the following restrictions according to formulas (1) and (2) apply to the contents of nitrogen and carbon, and the following restrictions according to formula (3) apply to the contents of oxygen, phosphorus and sulfur:

$$0.003\% \leq C+N \leq 0.5\% \text{ weight} \quad (1)$$

$$N/C(\text{wt. \%}) \leq 1.00 \text{ for } 0.07\% < C < 0.15\% \text{ (weight)} \quad (2)$$

$$O+P+S<0.10\% \text{ weight} \quad (3).$$

19 Claims, No Drawings

COBALT ALLOY FOR MEDICAL IMPLANTS AND STENT COMPRISING THE ALLOY

CROSS REFERENCE

The present application claims priority on U.S. provisional patent application No. 61/660,824 filed Jun. 18, 2012, which application is incorporated herein by reference.

TECHNICAL FIELD

The invention relates to cobalt-based alloys, the dominating deformation mechanism is twinning (TWIP effect). The invention further relates to a stent which is made entirely or partially of a cobalt alloy.

BACKGROUND

The implantation of stents has become established as one of the most effective therapeutic measures for the treatment of vascular diseases. Stents have the purpose of assuming a supporting function in hollow organs of a patient. For this purpose, stents featuring conventional designs have a filigree supporting structure comprising metal struts, which is initially present in compressed form for introduction in the body and is expanded at the site of the application. One of the main application areas of such stents is to permanently or temporarily widen and hold open vascular constrictions, particularly constrictions (stenosis) of coronary blood vessels. In addition, aneurysm stents are known, which are used primarily to seal the aneurysm.

Stents have a peripheral wall with sufficient load-bearing capacity to hold the constricted vessel open to the desired extent, and a tubular base body through which blood continues to flow without impairment. The peripheral wall is generally formed by a lattice-like supporting structure, which allows the stent to be introduced in a compressed state, in which it has a small outside diameter, all the way to the stenosis to be treated in the particular vessel and to be expanded there, for example by way of a balloon catheter, so far until the vessel has the desired, enlarged inside diameter. As an alternative, shape memory materials such as nitinol have the ability to self-expand when a restoring force keeping the implant at a small diameter is eliminated. The restoring force is generally applied to the material by a protective tube.

The stent has a base body made of an implant material. An implant material is a non-living material, which is employed for applications in medicine and interacts with biological systems. A basic prerequisite for the use of a material as implant material, which is in contact with the body area when used as intended, is the body friendliness thereof (biocompatibility). For the purpose of the present application, biocompatibility shall be understood to mean the ability of a material to induce an appropriate tissue reaction in a specific application. This includes an adaptation of the chemical, physical, biological, and morphological surface properties of an implant to the recipient's tissue with the aim of a clinically desired interaction. The biocompatibility of the implant material is also dependent on the temporal course of the reaction of the biosystem in which it is implanted. For example, irritations and inflammations occur in a relatively short time, which can lead to tissue changes. Depending on the properties of the implant material, biological systems thus react in different ways. According to the reaction of the biosystem, the implant materials can be divided into bioactive, bioinert and degradable/resorbable materials.

Implant materials comprise polymers, metallic materials, and ceramic materials (as coatings, for example). Biocompatible metals and metal alloys for permanent implants comprise, for example, stainless steels (such as 316L), cobalt-based alloys (such as CoCrMo cast alloys, CoCrMo forge alloys, CoCrWNi forge alloys and CoCrNiMo forge alloys), technical pure titanium and titanium alloys (such as cp titanium, TiAl6V4 or TiAl6Nb7) and gold alloys. In the field of biocorrodible stents, the use of magnesium or technical pure iron as well as biocorrodible base alloys of the elements magnesium, iron, zinc, molybdenum, and tungsten are proposed. The present invention relates to permanent implant materials, in particular cobalt-based alloys.

Stents desirably have the ability to tolerate extensive plastic strain and maintain the size or diameter thereof when they are expanded. In general, the ideal stent should:
- have a low profile; this includes the suitability of being crimped onto a balloon catheter;
- exhibit good expansion properties; when the stent is introduced in the lesion and the balloon is inflated, the stent should uniformly expand so as to adapt to the vessel wall;
- have sufficient radial strength and negligible recoil; once the stent has been placed, it should withstand the restoring forces of the atherosclerotic vessel wall and not collapse;
- have sufficient flexibility; the stent can thus also be delivered through vessels and stenoses having smaller diameters or narrow radii;
- have adequate radiopacity or MRI compatibility; the medical staff can thus assess the implantation and position of the stent in vivo;
- have low thrombogenicity; the material should be biocompatible and in particular prevent the deposition and agglutination of platelets; and
- have the option of releasing active agents; this is used in particular to prevent restenosis.

These requirements address in particular the mechanical properties of the material of which the stent is produced. The classic 316L, MP53N and L-605 materials used for constructing balloon-expandable stents have mechanical drawbacks which restrict the freedom in stent design development and in use:
(i) insufficient (tensile) strength and plastic expansion
As a result, the collapse pressure and radial strength are lower, necessitating thicker stent struts, which results in a thicker crimping profile and a larger loss of lumen during implantation, delays healing (endothelialization) into the vascular wall and restricts the freedom in the geometric stent design development. Thicker struts additionally make the stent more rigid, and in the crimped state the stent profile (diameter) increases, which reduces the flexibility around bends within the vascular system.
(ii) elastic limit Rp0.2 too high
This results in high elastic recovery, which worsens the crimpability, leads to a thicker crimp profile, lowers the stent retaining force on the balloon and causes higher recoil (loss of lumen due to expansion).

Moreover, the biocompatibility of the material must be ensured. Nickel has been suggested as causing allergies or local and systemic incompatibilities in some instances. A need therefore exists for nickel-free materials, or at least for materials having a low nickel content, for medical use.

Although various nickel-free implant constructions have been proposed, they leave various problems and deficiencies unresolved.

SUMMARY

A lasting need therefore exists for a metallic implant material which is suitable for producing stents.

Some invention embodiments relate to a cobalt-based alloy, which due to the following composition exhibits the Twinning inducted plasticity effect (TWIP effect) as the dominating deformation mechanism:

Cr: 13.0 to 30.0% by weight
Mn: 2.0 to 10.0% by weight
W: 2.0 to 18.0% by weight
Fe: 5.0 to 15.0% by weight
C: 0.002 to 0.5% by weight
N: 0 to 0.2% by weight
Si: 0 to 2.0% by weight
Ni: 0 to 5.0% by weight wherein the aforementioned alloying components, together with cobalt as the remainder and manufacturing-related impurities, add up to 100% by weight, and the following restrictions according to formulas (1) and (2) apply to the contents of nitrogen and carbon, and the following restrictions according to formula (3) apply to the contents of oxygen, phosphorus and sulfur:

$$0.003\% \leq C+N \leq 0.5\% \text{ (weight)} \quad (1)$$

$$N/C \leq 1.00 \text{ for } 0.07\% < C < 0.15\% \text{ (weight)} \quad (2)$$

$$O+P+S < 0.10\% \text{ (weight)} \quad (3).$$

The cobalt-based alloy used according to the invention is corrosion-resistant, friction wear-resistant and has high strength, which can be increased even further by suitable heat treating methods, and also has high ductility and excellent radiopacity. The alloying constituents stabilize the austenite such that the alloy is present, preferably completely, in austenitic (face-centered cubic; fcc.) modification, and they increase the stacking fault energy, whereby what is known as the TWIP (Twinning induced plasticity) effect, which is the deformation on the basis of twinning, is promoted, which allows strong hardening and high ductility at the same time.

The alloys used according to at least some embodiments of the invention exhibit very high tensile strength of >900 MPa, more particularly >1000 MPa, and particularly preferably >1100 MPa. The high strength makes it possible to produce thin structures in the stent design, which nonetheless give the stent high radial strength of >1.5 bar (150 kPa).

The alloys used according to at least some embodiments of the invention further exhibit a very pronounced strain-hardening behavior, which is expressed by the ratio Rp0.2/Rm between the elastic limit Rp0.2 and tensile strength Rm, which should be particularly small. Rp0.2/Rm should be <0.7, preferably <0.60, with <0.5 being particularly preferred. This property is particularly significant for controlling the deformation during the stent expansion. A homogeneous opening behavior is desirable, which depends not only on the mechanical properties of the material, but also the stent design, which in turn can be developed with greater freedom if the mechanical properties of the material allow.

The alloys according to at least some embodiments of the invention further exhibit excellent formability at room temperature. The degree of deformation (elongation at fracture, At) is >40%, preferably >50%, and more particularly >60%.

As a result, austenitic CoCrMnWFe alloys are provided, which at the most have a small nickel content and exhibit twinning induced plasticity (TWIP effect) as the predominant deformation mechanism. Stents produced from this material have higher radial strength, a homogeneous opening behavior, greater dilation reserves (nominal diameter+ 0.5 mm) and better crimpability (lower diameter), while having a reduced stmt cross-section (better endothelialization behavior) than conventional stents. Given the freedom of nickel or the low nickel content, strongly improved biocompatibility is attained. In addition, the resistance to pitting, abrasion and fretting is improved, in particular in situations in which two or more stents overlap each other.

The cause of the TWIP effect is the so-called stacking faults. Stacking faults can be imagined as a dislocation of atom layers that are regularly stacked on top of one another. A crystal structure can shear at such a stacking fault, whereby the crystal planes are stacked in exactly the reverse order starting at the dislocation. During shearing, a mirror plane is created, with the crystal regions appearing as mirror images on both sides of the plane. This is referred to as twinning. So as to form a twin, the so-called stacking fault energy (SFE) must be applied.

So as to attain the desired TWIP effect, two problems must be solved:

a) the austenitic state must be stabilized at room temperature; and b) the stacking fault energy of the alloy matrix should range between 15 and 50 mJ/m$^2$, and preferably between 20 and 30 mJ/m$^2$

DETAILED DESCRIPTION

Prior to the present invention, the problems described above within the present art had not been solved. The alloy according to the invention solves many of these problems by alloying the cobalt base with matching contents of corresponding suitable alloying elements, which stabilize the austenite, have high solubility and lower the stacking fault energy (for example W, Mo) or raise it (for example C, N, Ni). Some alloy embodiments achieve a stacking fault energy between 15 and 50 mJ/m$^2$, and some others between 20 and 30 mJ/m$^2$.

Elements used in cobalt alloys can be divided into two groups in terms of the effect thereof on the transition temperature from fcc to hexagonal close-packed (hcp), which is to say the effect thereof on the stabilization of the austenitic state. For example, Al, B, C, Cu, Fe, Mn, Nb, Ni, Sn, Ti and Zr lower the transition temperature from fcc to hcp and stabilize the austenitic state, while Sb, As, Cr, Ge, Ir, Mo, Os, Pt, Re, Rh, Ru, Si, Ta and W raise the transition temperature.

The elements C, N, Mn and optionally Ni are thus used to stabilize the austenitic state. In at least some embodiments, one or more of these is present, and in some embodiments each is present.

One embodiment of an alloy according to the invention contains C and N in total up to a maximum of 0.5% by weight and at least 0.003% by weight. The sum preferably ranges between 0.003 and 0.3% by weight, and more particularly between 0.003 and 0.1% by weight. Other concentrations may be used in other embodiments.

Carbon has an austenite-stabilizing effect and moreover is extremely effective at raising the stacking fault energy. Carbon additionally increases the strength by forming carbides. The carbon content should therefore not drop below 0.002% by weight in many embodiments. On the other hand, care must be taken to ensure that higher carbon contents do not lead to embrittlement and/or a decrease in the corrosion resistance due to excess carbide formation. It has been discovered that a useful balance between these competing parameters can be achieved by maintaining the carbon content below 0.5% by weight. The carbon content in many embodiments of the alloy is thus 0.002 to 0.5% by weight, preferably 0.002% to 0.15% by weight, and still more preferably 0.002 to 0.07% by weight. Other concentrations may be used in other embodiments.

Similarly, nitrogen also stabilizes the austenite, raises the stacking fault energy and increases the strength as well as hardness by forming nitride. In addition, nitrogen can prevent the formation of carbides if higher carbon contents are present. Depending on the carbon content, the content of nitrogen in many embodiments of the alloy can thus amount up to 0.2% by weight, preferably 0.15% by weight, and still more preferably 0.05% by weight. Nitrogen should be added at a ratio of 0.25 to 1, especially if the carbon content is between 0.07 and 0.15% by weight. Other concentrations may be used in other embodiments.

Nickel raises the stacking fault energy and thus is favorable in terms of forming the desired TWIP effect. For biocompatibility reasons, a content of Ni in many embodiments of the alloy must not exceed 5.0% by weight and preferably ranges between 2.0 and 5.0% by weight, and more particularly between 2.5 and 3.5% by weight. Other concentrations may be used in other embodiments.

Iron likewise stabilizes the austenite in cobalt starting at a content of approximately 5% by weight. Iron may be replaced completely or partially with manganese for further solid solution hardening. A content of Fe in many alloy embodiments is 5.0 to 15.0% by weight, and more particularly 9.5 to 10.5% by weight. Other concentrations may be used in other embodiments.

A content of Mn in many embodiments of the alloy is preferably 4.0 to 10.0% by weight, and more particularly 4.5 to 5.5% by weight. Other concentrations may be used in other embodiments.

Moreover, it is preferred if a content of Cr in the example alloy is 17.0 to 25.0% by weight, and more particularly 19.0 to 21.0% by weight. Chromium in solid solution increases the tensile strength. However, chromium also plays a key role in the corrosion and oxidation resistance. A high content of chromium means high corrosion resistance. The alloys according to the invention thus have high resistance to local corrosion, referred to as pitting.

Tungsten and molybdenum have approximately the same effect. Both elements increase the strength and improve the corrosion protection, but also counteract the stabilization of the austenite and additionally lower the stacking fault energy. In addition to solid solution hardening and the increase in friction resistance due to tungsten, the increased material density of tungsten especially when used as a vascular support is advantageous, because good radiopacity is achieved. It is therefore particularly preferred if a content of W in the alloy is 9.0 to 18.0% by weight, and more particularly 14.5 to 15.5% by weight. Other concentrations may be used in other embodiments.

Molybdenum counteracts the stabilization of the austenite and, together with cobalt, forms brittle intermetallic phases, which lower the ductility. Many embodiments of the alloy are therefore free of molybdenum.

A content of Si in the example alloy is preferably less than 0.7% by weight, and more particularly the content is 0.05 to 0.5% by weight. Other concentrations may be used in other embodiments.

Many alloy embodiments are additionally largely free of Ti, Ta, Nb and Al, and at least some are completely free of these materials.

Impurities, notably O, S and P, may reduce the ductility, both in the form of oxides, sulfides and phosphides ($Fe_3P$) and in solid solution. The content in each case should therefore be below 0.5% by weight. In total, the content of O, S and P should therefore be below 0.10% by weight, and more preferably below 0.07% by weight.

The invention further relates to the use of the aforementioned cobalt alloy for producing a stent.

The alloys can be produced analogously to the customary production methods for cobalt-based alloys.

It will also be appreciated that embodiments of the invention include stents and other implants. Stents of the invention may include features such as a generally tubular base body. Stents embodiments may include a filigree supporting structure comprising metal struts, which is initially present in compressed form for introduction in the body and is expanded at the site of the application. The stents have a peripheral tubular or cylindrical wall with sufficient load-bearing capacity to hold the constricted vessel open to the desired extent, and a tubular base body through which blood continues to flow without impairment. The peripheral wall is generally formed by a lattice-like supporting structure, which allows the stent to be introduced in a compressed state, in which it has a small outside diameter, all the way to the stenosis to be treated in the particular vessel and to be expanded there, for example by way of a balloon catheter, so far until the vessel has the desired, enlarged inside diameter. One or more coatings may be provided, for example, to carry and elute a drug. Some or all metal elements of stents of the invention may be made of an alloy of the invention. Various features and elements of such stents are generally known (other than the alloy construction), and need not be discussed or illustrated herein for sake of brevity.

Exemplary Embodiment 1

Co-20Cr-15W-10Fe-5Mn-3Ni-0.05C

Mechanical properties in the recrystallized state after annealing at approximately 1200° C. with subsequent water cooling:

Rp0.2=500-550 MPa

Rm=1000-1050 MPa

A>60%

Exemplary Embodiment 2

Co-22Cr-14W-8Fe-8Mn-0.15Si-0.15N-0.07C

Mechanical properties in the recrystallized state after annealing at approximately 1200° C. with subsequent water cooling:

Rp0.2=520-570 MPa

Rm=1100-1150 MPa

A>50%

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A cobalt alloy comprising a tensile strength of greater than 900 MPa and having the following composition:
   Cr: 13.0 to 30.0% by weight
   Mn: 2.0 to 10.0% by weight
   W: 2.0 to 18.0% by weight
   Fe: 5.0 to 15.0% by weight
   C: 0.002 to 0.5% by weight
   N: 0 to 0.2% by weight
   Si: 0 to 2.0% by weight
   Ni: 2.0 to 3.5% by weight
   Co: balance,
   wherein the aforementioned alloying components and manufacturing-related impurities add up to 100% by weight, and the following restrictions according to formulas (1) and (2) apply to the contents of nitrogen and carbon, and the following restrictions according to formula (3) apply to the contents of oxygen, phosphorus and sulfur:

$0.003\% \leq C+N \leq 0.5\%$ (by weight) (1)

$N/C(\text{wt. }\%) \leq 1.00$ for $0.07\% < C < 0.15\%$ (by weight) (2)

$O+P+S < 0.10\%$ (by weight) (3), wherein the alloy is free from Mo.

2. The alloy according to claim 1, wherein a content of Cr in the alloy is 17.0 to 25.0% by weight.
3. The alloy according to claim 1, wherein a content of Mn in the alloy is 4.0 to 10.0% by weight.
4. The alloy according to claim 1, wherein a content of W in the alloy is 9.0 to 18.0% by weight.
5. The alloy according to claim 1, wherein a content of Fe in the alloy is 9.5 to 10.5% by weight.
6. The alloy according to claim 1, wherein a content of Si in the alloy is less than 0.7% by weight.
7. The alloy according to claim 1, wherein a content of C in the alloy is 0.002 to 0.15% by weight.
8. The alloy according to claim 1, wherein a content of C in the alloy is 0.07 to 0.15% by weight and N/C (wt. %) ranges between 0.25 and 1.
9. The alloy according to claim 1, wherein a content of Ni in the alloy is 2.5 to 3.5% by weight.
10. The alloy according to claim 1, wherein a content of Ni in the alloy is 2.5 to 3.5% by weight, and the total weight % of C and N together is between 0.003 and 0.3.
11. The alloy according to claim 1, wherein the total weight % of C and N together is between 0.003 and 0.1.
12. The alloy according to claim 1 wherein Cr is present in a weight % of between 19.0 and 21.0.
13. The alloy according to claim 1 wherein W is present in a weight % of between 14.5% to 15.5%.
14. The alloy according to claim 1 wherein the Si is present in a weight % between 0.05 to 0.5%.
15. The alloy according to claim 1 wherein the alloy is free of Ti, Ta, Nb and Al.
16. The alloy according to claim 1 wherein the content of O, S and P in alloy is below 0.07% weight in total.
17. A cobalt alloy, having the following composition:
    Cr: 13.0 to 30.0% by weight
    Mn: 2.0 to 10.0% by weight
    W: 2.0 to 18.0% by weight
    Fe: 5.0 to 15.0% by weight
    C: 0.002 to 0.5% by weight
    N: 0 to 0.2% by weight
    Si: 0 to 2.0% by weight
    Ni: 2.0 to 3.5% by weight
    Co: balance,
    wherein the aforementioned alloying components and manufacturing-related impurities add up to 100% by weight, and the following restrictions according to formulas (1) and (2) apply to the contents of nitrogen and carbon, and the following restrictions according to formula (3) apply to the contents of oxygen, phosphorus and sulfur:

$0.003\% \leq C+N \leq 0.5\%$ (by weight) (1)

$N/C(\text{wt. }\%) \leq 1.00$ for $0.07\% < C < 0.15\%$ (by weight) (2)

$O+P+S < 0.10\%$ (by weight) (3), wherein the alloy is free from Mo; and
    wherein the alloy has a stacking fault energy between 20 and 30 mJ/m$^2$.

18. A stent comprising a filigree support structure made entirely or partially of a cobalt alloy comprising a tensile strength of greater than 900 MPa and having the following composition:
    Cr: 13.0 to 30.0% by weight
    Mn: 2.0 to 10.0% by weight
    W: 2.0 to 18.0% by weight
    Fe: 5.0 to 15.0% by weight
    C: 0.002 to 0.5% by weight
    N: 0 to 0.2% by weight
    Si: 0 to 2.0% by weight
    Ni: 0 to 3.5% by weight
    Co: balance,
    wherein the aforementioned alloying components and manufacturing-related impurities add up to 100% by weight, and the following restrictions according to formulas (1) and (2) apply to the contents of nitrogen and carbon, and the following restrictions according to formula (3) apply to the contents of oxygen, phosphorus and sulfur:

$0.003\% \leq C+N \leq 0.5\%$ (wt.) (1)

$N/C(\text{wt. }\%) \leq 1.00$ for $0.07\% < C < 0.15\%$ (wt.) (2)

$O+P+S < 0.10\%$ (wt.) (3)

wherein the alloy is free from Mo.

19. A stent as defined by claim 18, wherein the stent further includes a generally tubular shaped base body that is made entirely of the alloy.

* * * * *